(12) United States Patent
Kuo-Petravic et al.

(10) Patent No.: US 7,170,966 B2
(45) Date of Patent: Jan. 30, 2007

(54) PRACTICAL IMPLEMENTATION OF A CT CONE BEAM ALGORITHM FOR 3-D IMAGE RECONSTRUCTION AS APPLIED TO NONDESTRUCTIVE INSPECTION OF BAGGAGE, LIVE LABORATORY ANIMAL AND ANY SOLID MATERIALS

(76) Inventors: Gioietta Kuo-Petravic, P.O. Box 1761, Twain Harte, CA (US) 95383; Horst Bruning, Exxim Computine Corp, 3825 Hopyard Rd., Suite 119, Pleasanton, CA (US) 94588; Marijan Petravic, P.O. Box 1761, Twain Harte, CA (US) 95383

( * ) Notice: Subject to any disclaimer, the term of this patent is extended or adjusted under 35 U.S.C. 154(b) by 311 days.

(21) Appl. No.: 10/899,708

(22) Filed: Jul. 26, 2004

(65) Prior Publication Data

US 2005/0041771 A1 Feb. 24, 2005

Related U.S. Application Data

(66) Substitute for application No. 60/492,676, filed on Aug. 6, 2003.

(60) Provisional application No. 60/492,469, filed on Aug. 5, 2003.

(51) Int. Cl.
*A61B 6/03* (2006.01)

(52) U.S. Cl. .................. 378/4; 378/10; 378/20

(58) Field of Classification Search .......... 378/4, 378/10, 19, 20
See application file for complete search history.

(56) References Cited

U.S. PATENT DOCUMENTS

| | | | | |
|---|---|---|---|---|
| 5,119,408 A | * | 6/1992 | Little et al. | 378/4 |
| 5,124,914 A | * | 6/1992 | Grangeat | 378/50 |
| 5,278,884 A | * | 1/1994 | Eberhard et al. | 378/4 |
| 5,375,156 A | * | 12/1994 | Kuo-Petravic et al. | 378/9 |

(Continued)

FOREIGN PATENT DOCUMENTS

DE 19542762 A1 * 5/1997

(Continued)

OTHER PUBLICATIONS

Clack et al., A Filtered-Backprojection Cone-beam Algorithm for General Orbits with Implementation Details for the Two-Orthogonal-Circles Orbit, Oct. 31-Nov. 6, 1993, Nuclear Science Symposium and Medical Imaging Conference, IEEE Conference Record, vol. 3, pp. 1590-1594.*

(Continued)

*Primary Examiner*—Edward J. Glick
*Assistant Examiner*—John M. Corbett

(57) ABSTRACT

This invention uses the cone beam CT (Computer Tomography) principle to obtain nondestructive image of any object. For good reconstruction datasets from 2 orthogonal planes about the object are required in order to augment the signal relative to the polar artifacts of a standard Feldkamp reconstruction algorithm. Here, we suggest a practical way of implementing the 2 orthogonal planes theory by replacing the 2 gantry rotations by 2 rotations of only one fixed gantry and one movement of the object position, making it simple and low cost. This method is applied to the non-intrusive inspection of baggage or imaging of mice for pharmaceutical purposes where the object has to remain in a horizontal plane throughout the procedure. This algorithm can also be applied to nondestructive testing of any solid materials, for example: imperfections in semi-conductors, electronic components, composite materials etc.

9 Claims, 15 Drawing Sheets

U.S. PATENT DOCUMENTS 5,999,587 A * 12/1999 Ning et al. ..................... 378/4
6,584,170 B2 * 6/2003 Aust et al. ..................... 378/57

OTHER PUBLICATIONS

Zeniya et al., Image improvement in pinhole SPECT using complete data acquisition combined with statistical image reconstruction, Aug. 2004, Proceedings of the International Workshop on Quantition in Biomedical Imaging with PET and MRI, vol. 1265, pp. 101-105.*

Soimu et al., Circular isocentric cone-beam trajectories for 3-D image reconstructions using FDK Algorithm, Jul. 31-Aug. 5, 2004, Proceedings of Medicon and Health Telematics 2004 Conference.*

* cited by examiner

Scan 1

Scan 1

Scan 2

Scan 2

Scan 1

Scan 2

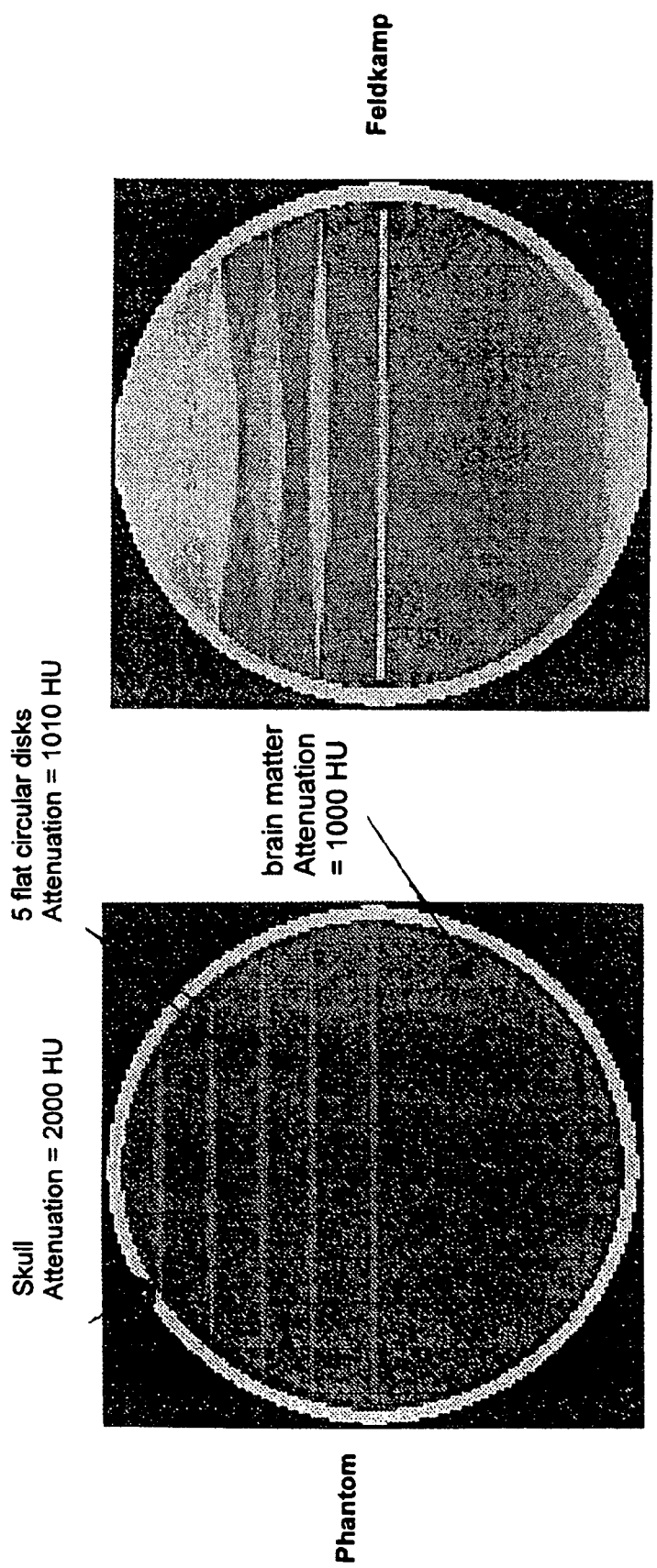
Figure 8a Reconstruction of phantom of Figure 7 using Feldkamp single scan (G1)
Figure 7 Grey level image of a computer phantom consisting of 5 horizontal thin 2 voxels wide flat disks.

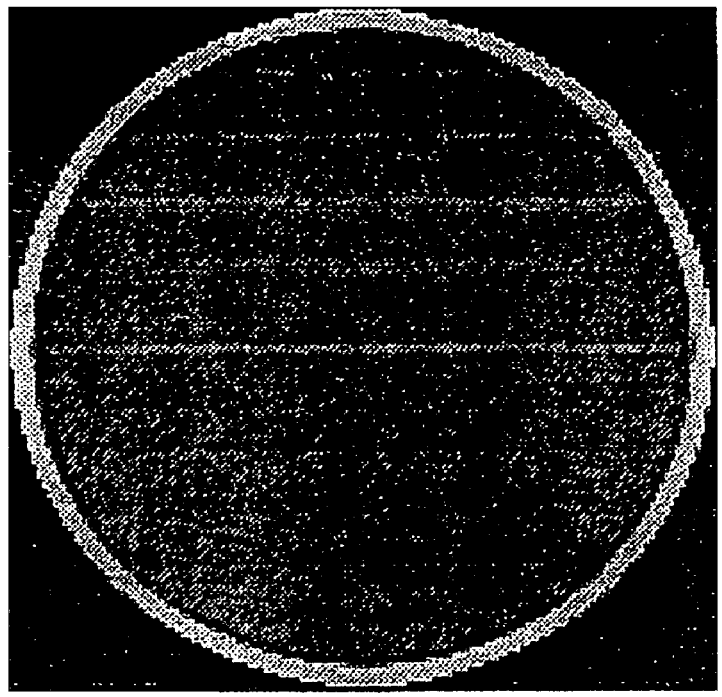
Figure 8b Reconstruction of phantom of Figure 7 using 2 scans (G2)
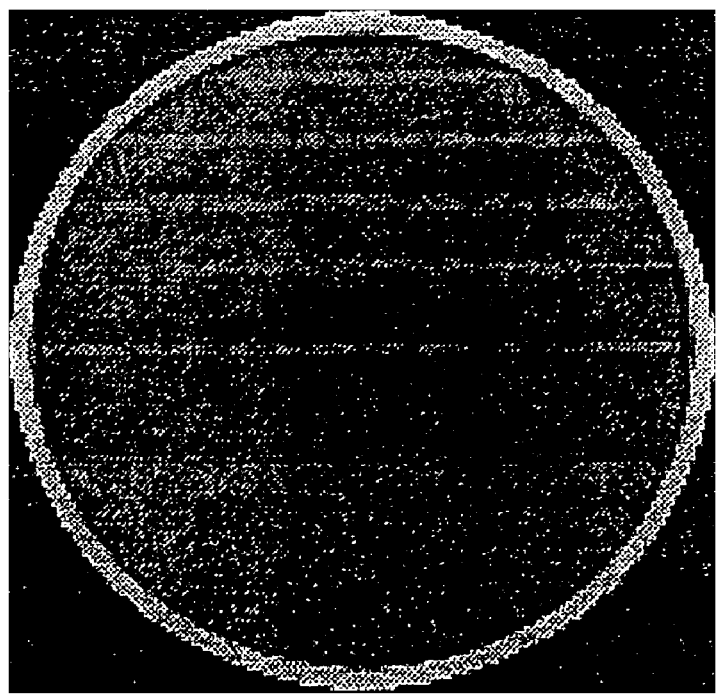
Figure 8c Reconstruction of phantom of Figure 7 using 3 scans (G3)

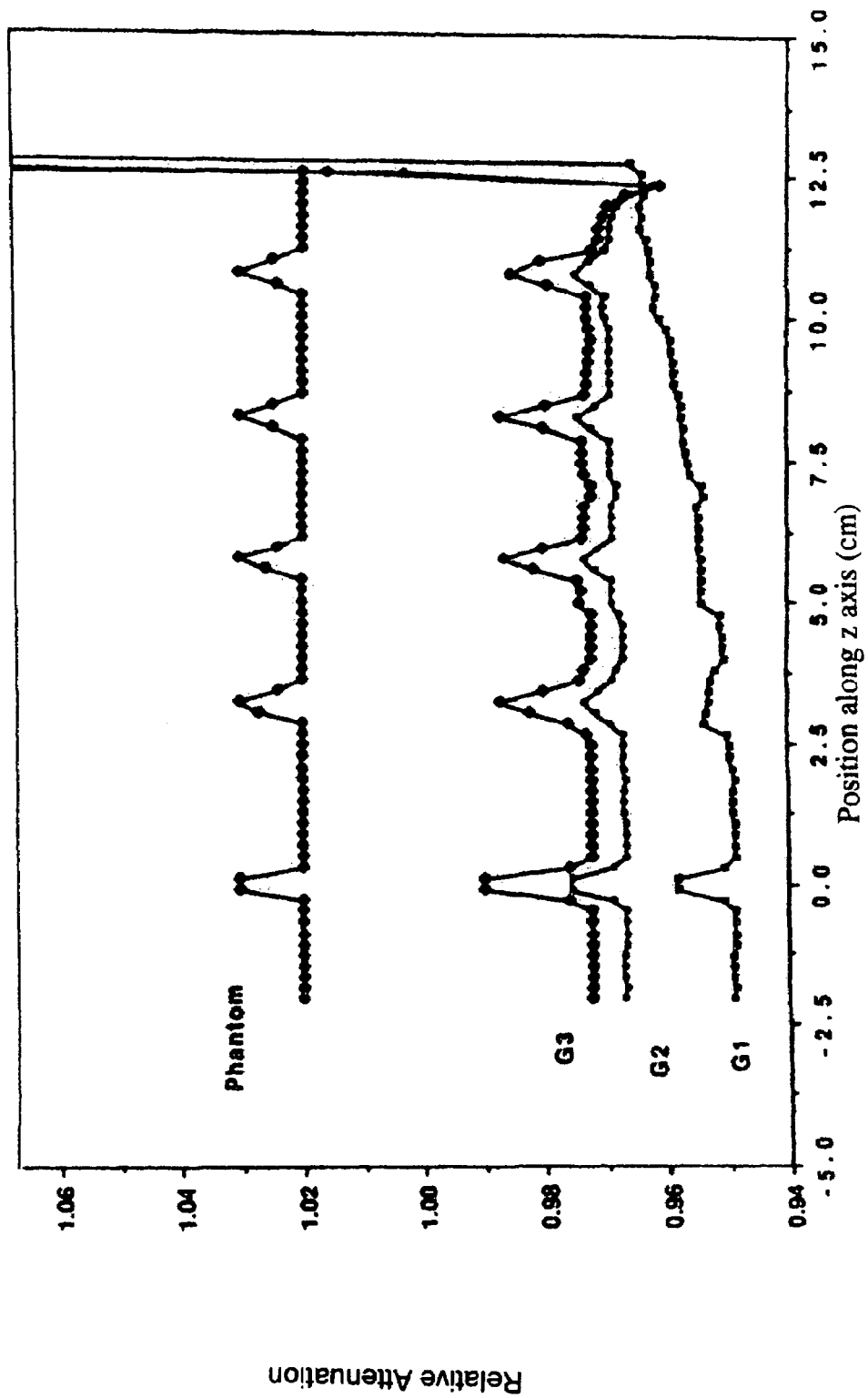
Figure 9a A vertical line through the vertical (coronal) plane perpendicular to the axis of the source and dtector assembly at x = y = 0.1 cm. Phantom Attenuation = 1010 HU

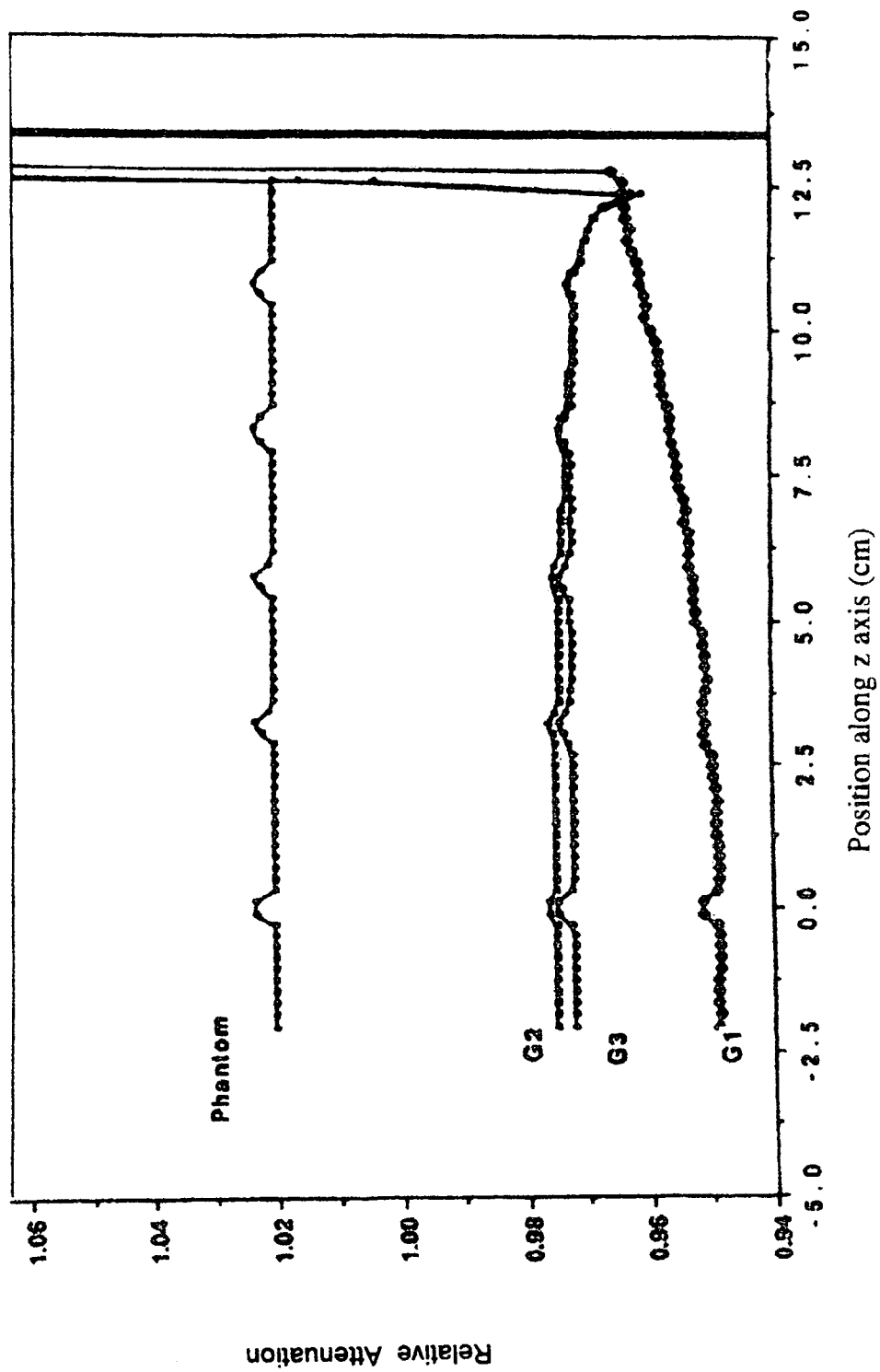
Figure 9b  A vertical line through the vertical (coronal) plane perpendicular to the axis of the source & detector assembly at x = y = 0.1 cm. Phantom Attenuation = 1003 HU.

Scan 1

Scan 1

Scan 2

Scan 2

PRACTICAL IMPLEMENTATION OF A CT CONE BEAM ALGORITHM FOR 3-D IMAGE RECONSTRUCTION AS APPLIED TO NONDESTRUCTIVE INSPECTION OF BAGGAGE, LIVE LABORATORY ANIMAL AND ANY SOLID MATERIALS

CROSS-REFERENCE TO RELATED APPLICATIONS

This non-provisional utility patent application describes an alternative and new practical procedure for achieving the same high resolution images of a previous patent application by Gioietta Kuo-Petravic & Rolf Hupke of U.S. Pat. No. 5,375,156 of Dec. 20, 1994 entitled:
"Method And Apparatus For 3-D Computer Tomography"
See also provisional patent: U.S. PTO No. 60/492,469, 08/05/2003:
"A Practical Implementation Of A CT Cone Beam Algorithm For 3-D Image Reconstruction For Nondestructive Inspection Of Baggage"
by Gioietta Kuo-Petravic & Marijan Petravic
See also provisional patent: U.S. PTO No. 60/492,676 08/06/2003
"A low cost practical implementation of a CT cone beam algorithm for 3-D image reconstruction for non-destructive testing of solid objects"
by Gioietta Kuo-Petravic & Marijan Petravic

STATEMENT REGARDING FEDERALLY SPONSORED RESEARCH OR DEVELOPMENT

This application has been funded solely by the personal resources of the inventors: Gioietta Kuo-Petravic, Horst Bruning and Marijan Petravic.
And is NOT made under federally sponsored research.

REFERENCE TO SEQUENCE LISTING, A TABLE, OR A COMPUTER PROGRAM LISTING COMPACT DISK APPENDIX

Not Applicable. No compact disk submitted

BACKGROUND OF THE INVENTION

The non-intrusive method of obtaining information on the attenuation of objects inside a body by the use of a X-ray beam—commonly referred to as CT (Computer Tomography), has been well developed ever since its invention in the early 1970's, particularly in the medical field. In the past, CT has been applied to fan beam geometry in a 2-D plane. That is, by measuring the attenuation of x-rays through a 2-D object with a source-detector assembly which rotates in the plane of the object about an axis in the perpendicular direction to that plane, it is possible to reconstruct an image of that object.

So far, almost all medical CT scanners use a 2-D geometry, which means that a 3-D view would require the composition of many slices of 2-D data. This is by its very nature a slow process and attention of the CT industry has now seriously turned to cone beam data acquisition which could be an order of magnitude faster than fan beam. However, there are difficulties in going 3-D:

The 2-D array of detectors become prohibitively expensive if conventional solid state x-ray detectors are used. However there exist now proprietary methods which Bio-Imaging Research (BIR) Inc among others have developed that would bring down the cost.

There exists no readily implementable 3-D image reconstruction algorithm which gives a satisfactory image. In the early 1990s, some theoretical physicists in the CT field, working independently, have come to the conclusion that for a good image of a 3-D object using cone beam geometry, data has to be collected around the 3-D object in 2 orthogonal planes rather than in just one plane, as proposed by Feldkamp et al (1). The basis of the 2 orthogonal plane algorithm is founded on the basic physical fact that with one plane, we collect only line integrals near to the rotation plane and there are no line integrals in other directions. For a good 3-D reconstruction, information contained in the line integral data near another plane orthogonal to the first plane is necessary for a more complete high resolution image. The improvement of the 2 orthogonal scan can be also understood in terms of sampling: Taking a second scan improves the signal/noise ratio by a factor of 2, hence lifting the image of the object above noise, which in this case are artifacts.

We Apply this 2 Orthogonal Scan Method here to 2 Cases:
1) The non-intrusive inspection of baggage or imaging of any other object which has to remain in a horizontal position throughout the procedure and can not be turned through 90° into the vertical direction for the second scan because of the possible shifting of objects inside the object. Other applications of this algorithm include the 3-D imaging of an anaesthetized mouse or other experimental animal for pharmaceutical purposes.
2) For the testing of any solid materials which can be turned into the vertical position for the second scan.

The references dealing with 3-D reconstruction which are relevant to this application are:
(1) L. A. Feldkamp. L. C. Davis and Kress, J. Opt. Soc. Am., 1, 1984
(2) H. Kudo and Y. Saito, J. Opt. Soc. Am., 7, 1990.
(3) B. Smith, Opt. Eng., 29, 1990.
(4) R. Clack and M. Defrise, 1993 IEEE Nuclear Science and Medical Imaging Symposium, San Francisco. IEEE Service Center, Piscataway N.J. 1590–1994, 1994.

BRIEF SUMMARY OF INVENTION

With the exception of reference (1), which describes a basic cone beam one circle scan algorithm, all the references above from (2) to (5) have made suggestions on the 2 orthogonal scan configuration. FIG. 1 shows the principal features of the geometry of 2 circle scan. Scan 1 has a gantry rotation in the (x, y, z=0) plane and by itself it constitutes the standard Feldkamp algorithm. The addition of another gantry rotating in an orthogonal direction in (x=0, y, z) plane provides line integrals which are basically in planes orthogonal to that of the first scan. Hence we have made a more complete sampling of the object, leading to much better resolution.

Although the advantages of 2 orthogonal plane scanning have been known for more than 10 years, no scanners have been built using this principle. This is because it is impractical and expensive to have 2 rotating gantries each containing its cone beam source-detector assembly operating in 2 perpendicular planes.

In this application, we suggest two alternative new, practical and simple procedure of obtaining the same good image as described by Kuo-Petravic & Hupke in U.S. Pat. No. 5,375,156, December 1994, where the two rotating source-detector assemblies, FIG. 1, are replaced by:

Application

For non-intrusive inspection of baggage or imaging of mice. Two rotations of one fixed rotating gantry and a 90° or 270° rotation of the object in a horizontal plane for objects which have to remain in a horizontal plane Application B For the nondestructive testing of solid objects. A rotation of the object through 90° or 270° by means of pivots into the vertical position in between two rotations of a table supporting the object.

Geometry for Step 1 uses the standard geometry of Feldkamp algorithm: rotation in one plane only. The gantry consists of a rotating x-ray source-detector assembly in the (x-z) plane rotating about the y axis.

Figure 3:
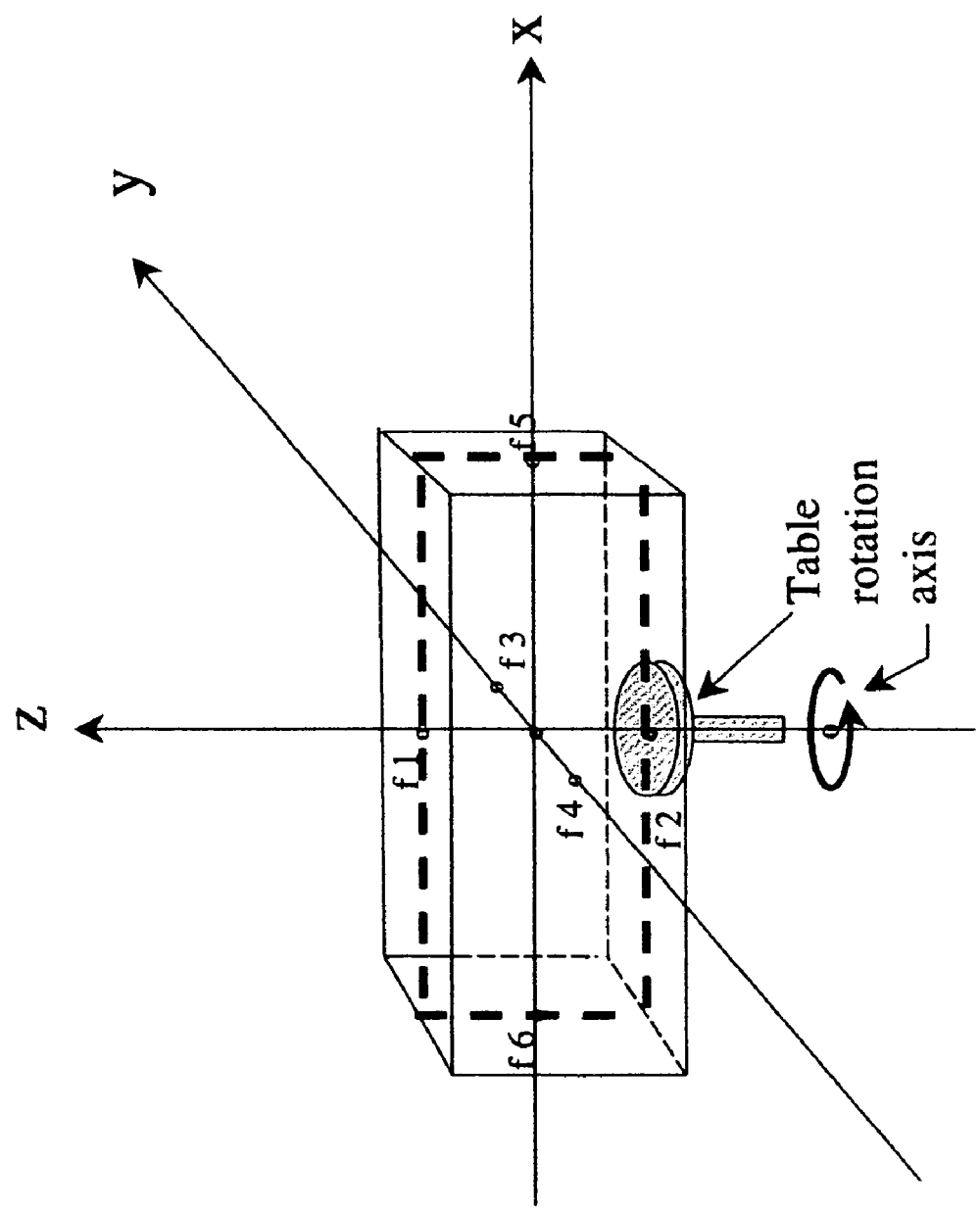

FIG. 3 For application A

Schematic drawing of the object, assumed to be a rectangular parallelepiped for purposes of illustration, in the position of Step 1.

Figure 4:
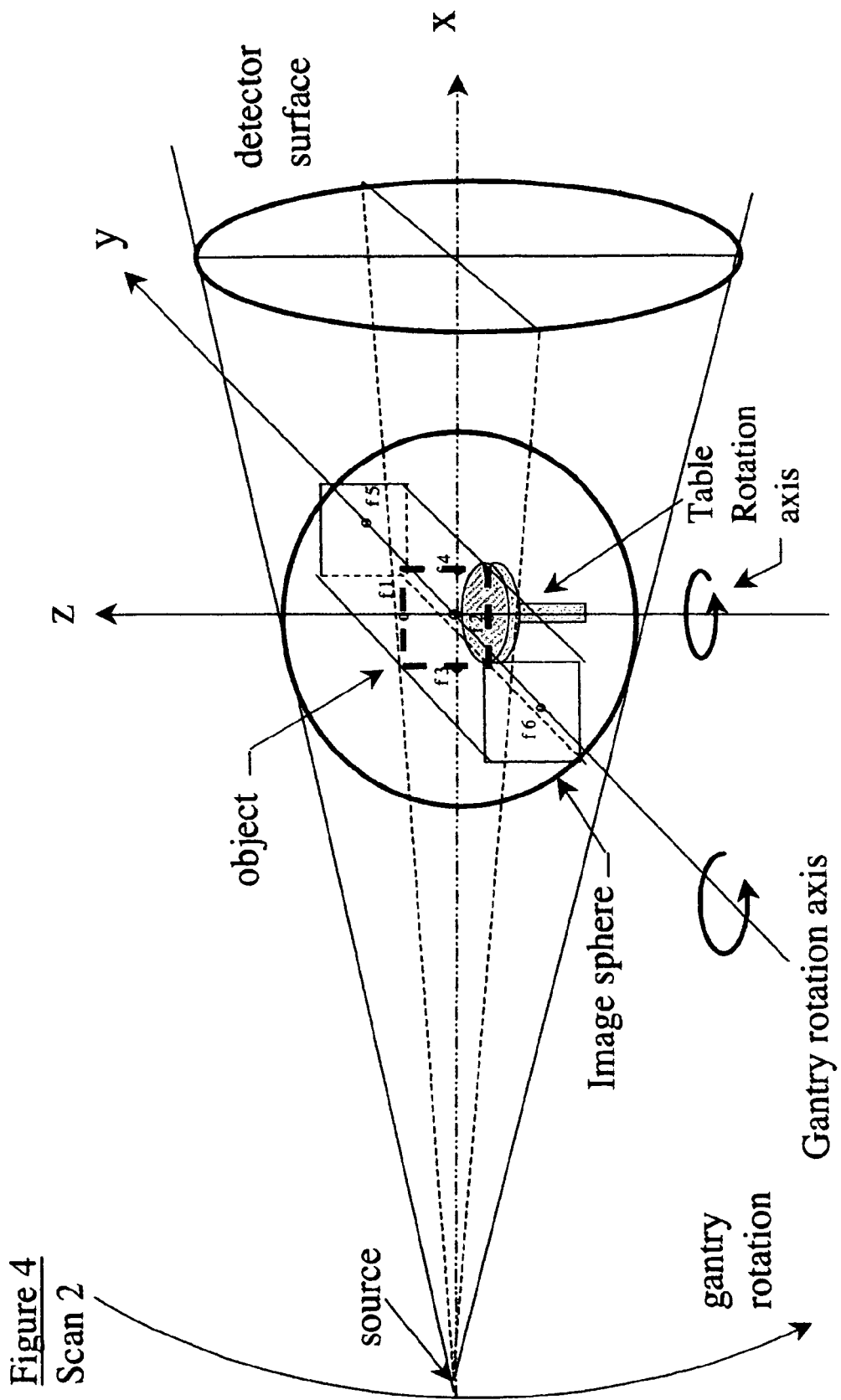

FIG. 4 For application A

Geometry for scan 2. After the object has been rotated through 90° or 270° about the z axis in the horizontal x-y plane, another rotation of the same gantry is performed.

Figure 5:
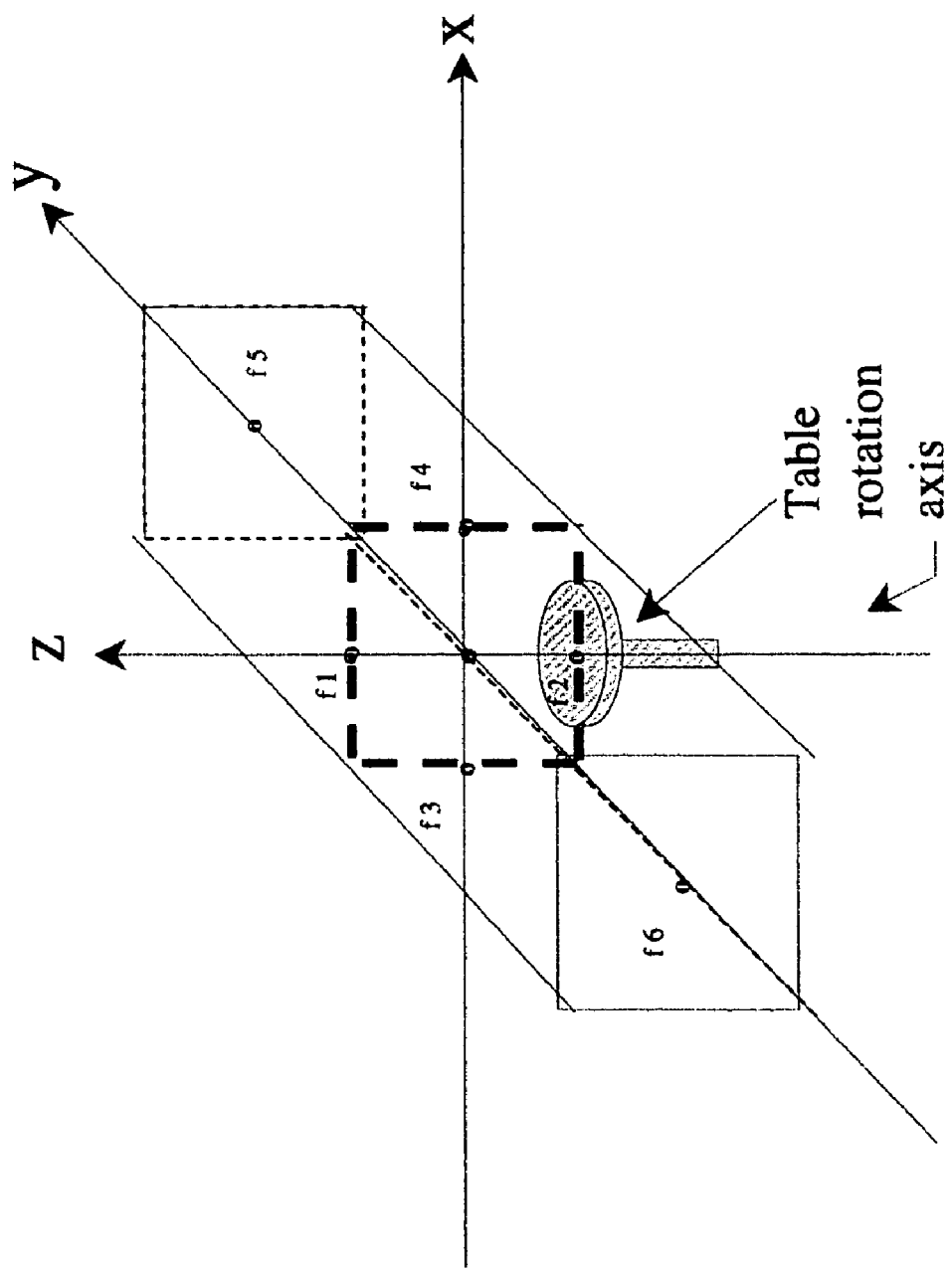

FIG. 5 For application A

Schematic drawing of the object in the position of Step 2 for the geometry of scan 2.

Figure 6A:
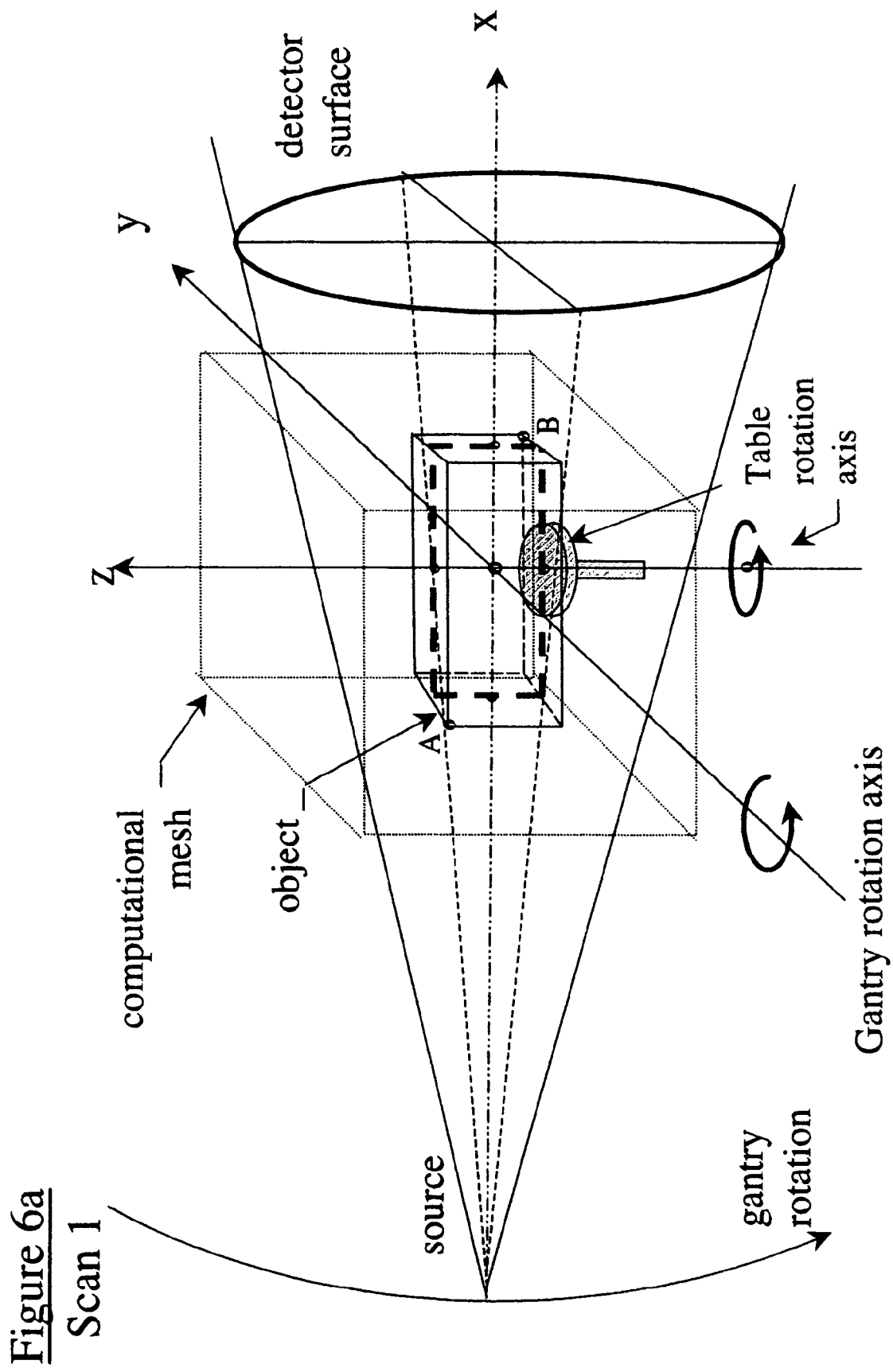

FIG. 6a For application A

Geometry of scan 1 with the 'long' side of the object along the x-axis and the computational mesh over the whole of the object.

Figure 6B:
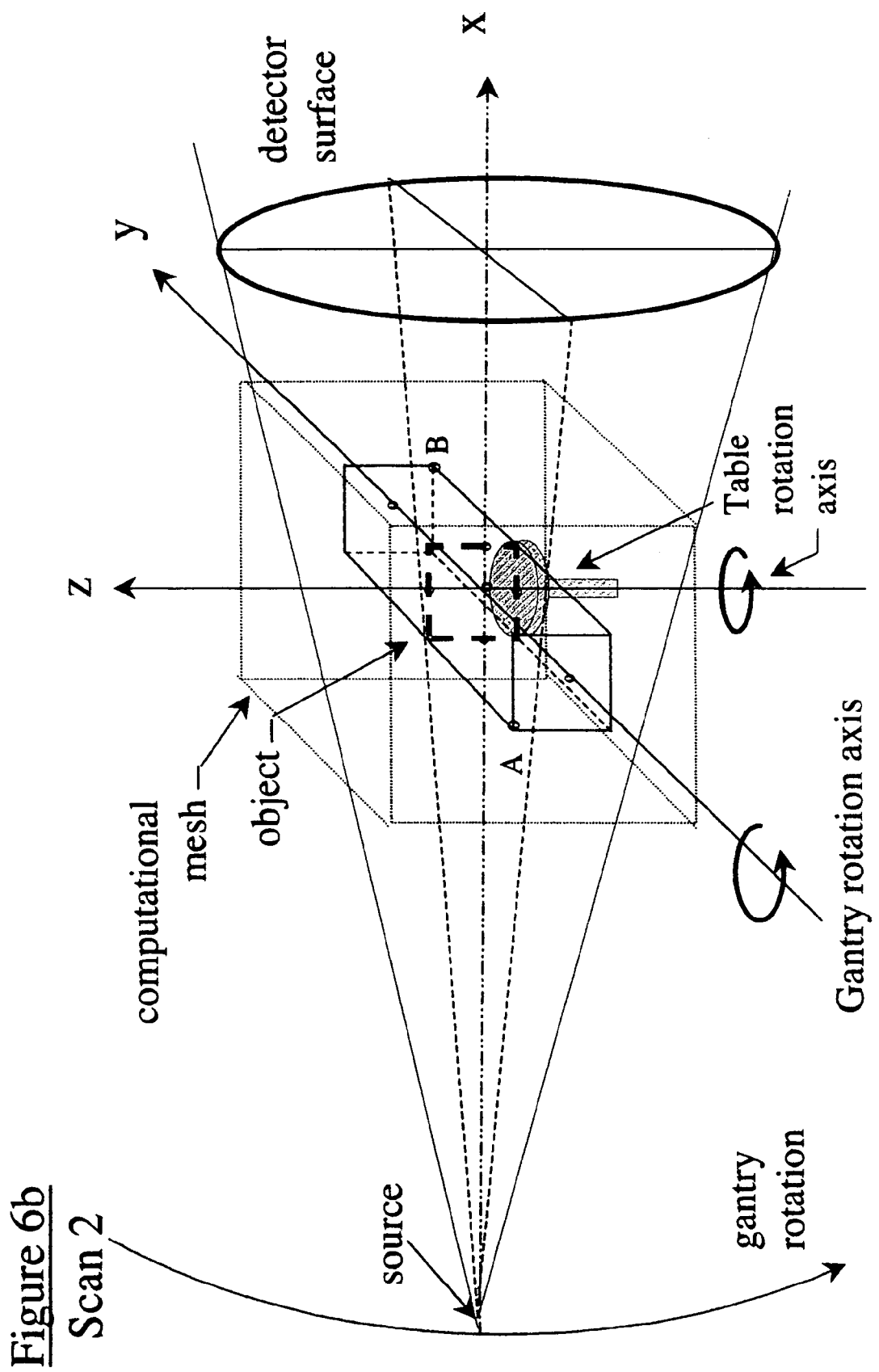

FIG. 6b For application A

Geometry of scan 2 with the 'long' side of the object along the y-axis with the computational mesh over the whole of the object.

FIG. 7 For application A

Grey level images of a computer phantom consisting of 5 horizontal thin 2 voxels wide flat disks at 1010 HU with skull at 2000 HU and watery matter at 1010 HU. The plane of the image shown is a vertical plane perpendicular to the axis of the source and the detector system along the x axis, that is the (y, z) plane, also called coronal plane in medical terminology.

FIG. 8a For application A

Gray level image of a single scan (G1) Feldkamp reconstruction of the phantom in the coronal plane in FIG. 7.

FIG. 8b For application A

Gray level image of the two scan (G2) reconstruction of the phantom in the coronal plane in FIG. 7.

FIG. 8c For application A

Figure 1:
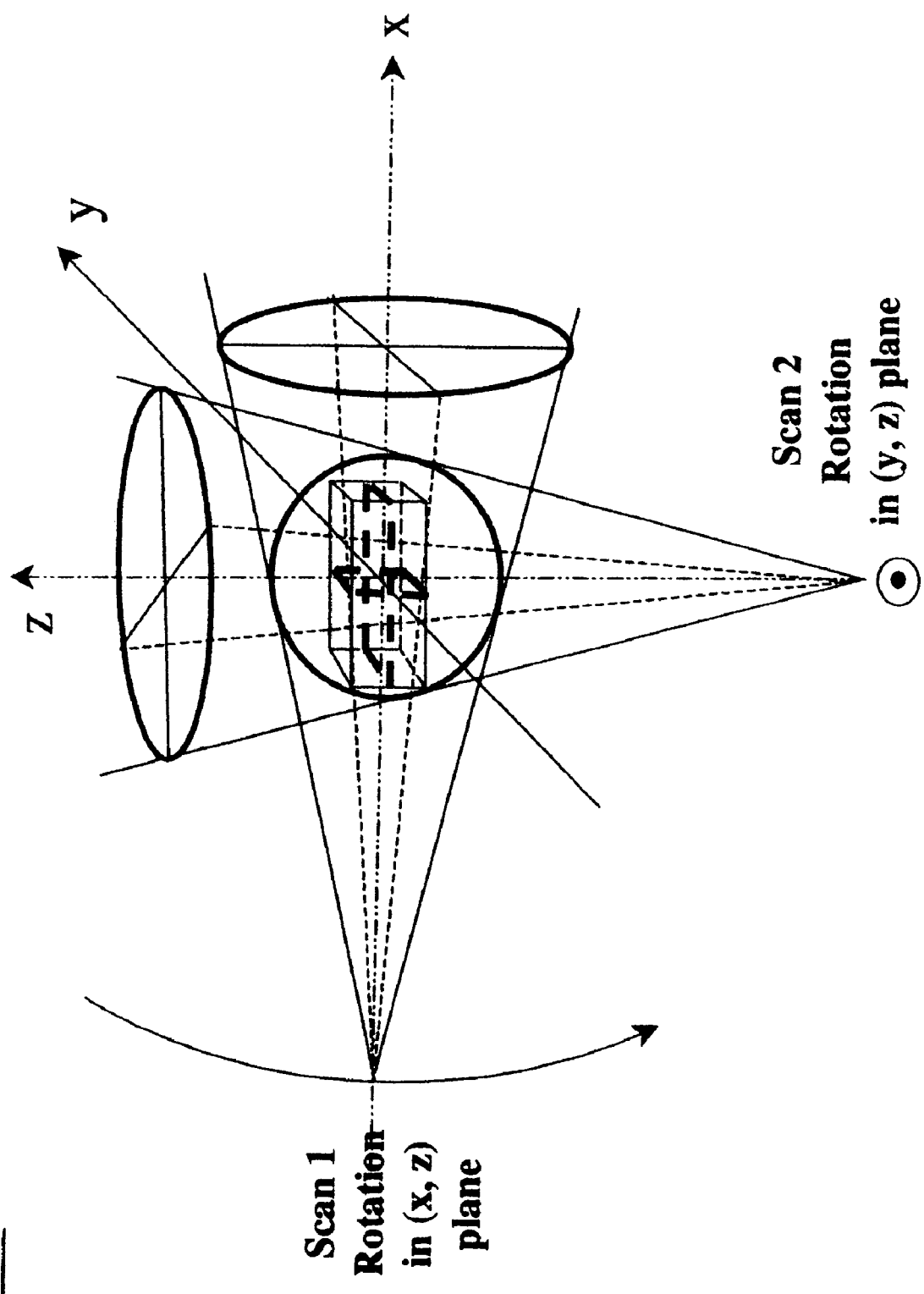
FIG. 1. Geometry of the 2 orthogonal scan, with 2 gantries as described in the patent by Gioietta Kuo-Petravic & Rolf Hupke of U.S. Pat. No. 5,375,156 of Dec. 20, 1994.

With the addition of yet another gantry orthogonal to the 2 gantries of FIG. 1, gray level image of 3 consecutive scans (G3) reconstruction of the phantom in the coronal plane in FIG. 7.

FIG. 9a For application A

Attenuation ratio=1.01. Linear plot in the vertical z direction through the coronal planes of FIGS. 7, 8a, 8b, 8c at x=y=0.1 cm. Attenuation of disk=1010 HU.

FIG. 9b For application A

Attenuation ratio=1.003. Linear plot in the vertical z direction through the coronal planes of FIGS. 7, 8a, 8b, 8c at x=y=0.1 cm. Attenation of disk=1003 HU.

Figure 10:
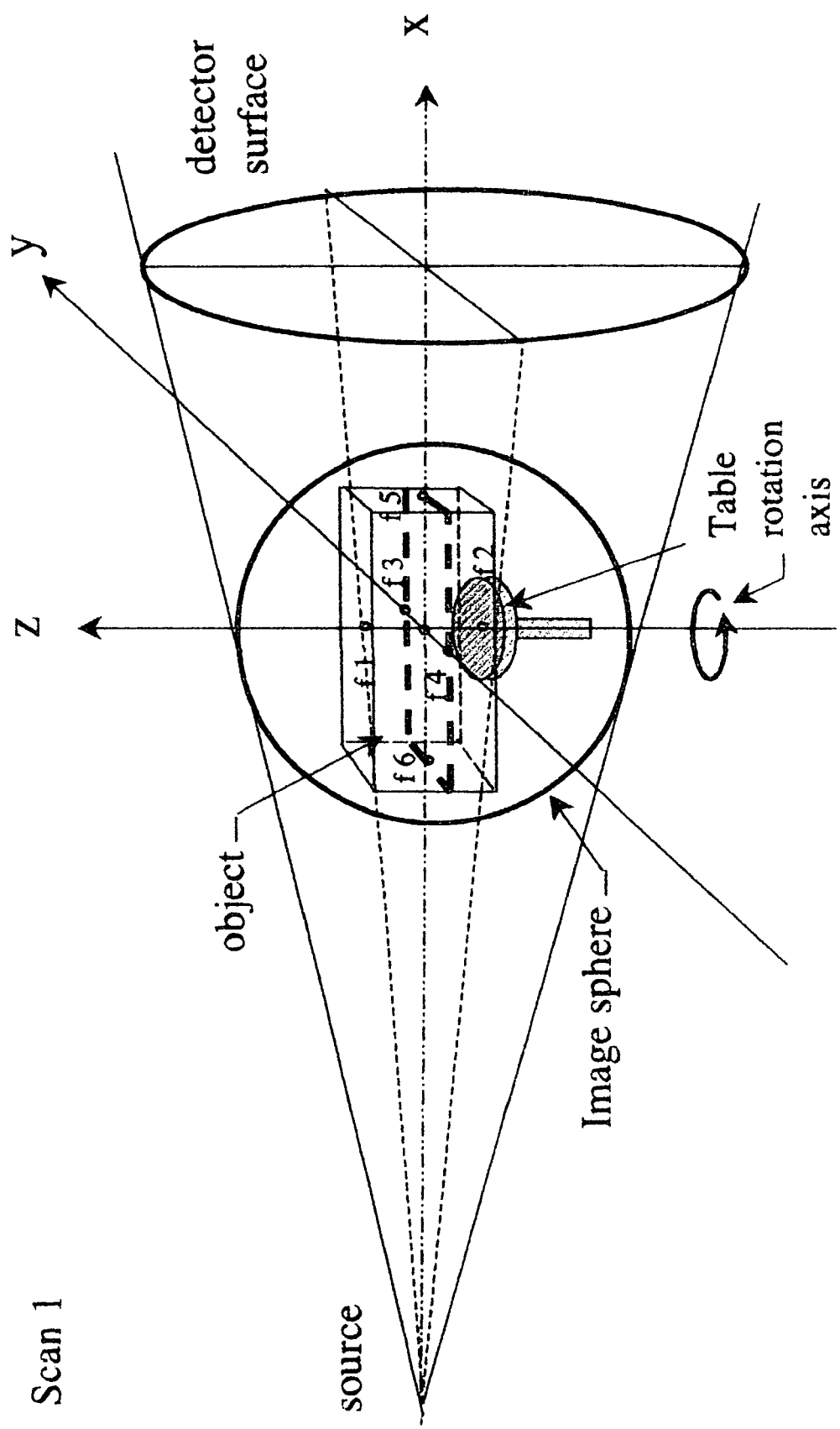

FIG. 10 For Application B

Geometry for Step 1 uses the standard geometry of the Feldkamp algorithm. The object is rotated in (x-y) plane about the z-axis while the source and detector system remains fixed on the x-axis.

Figure 11:
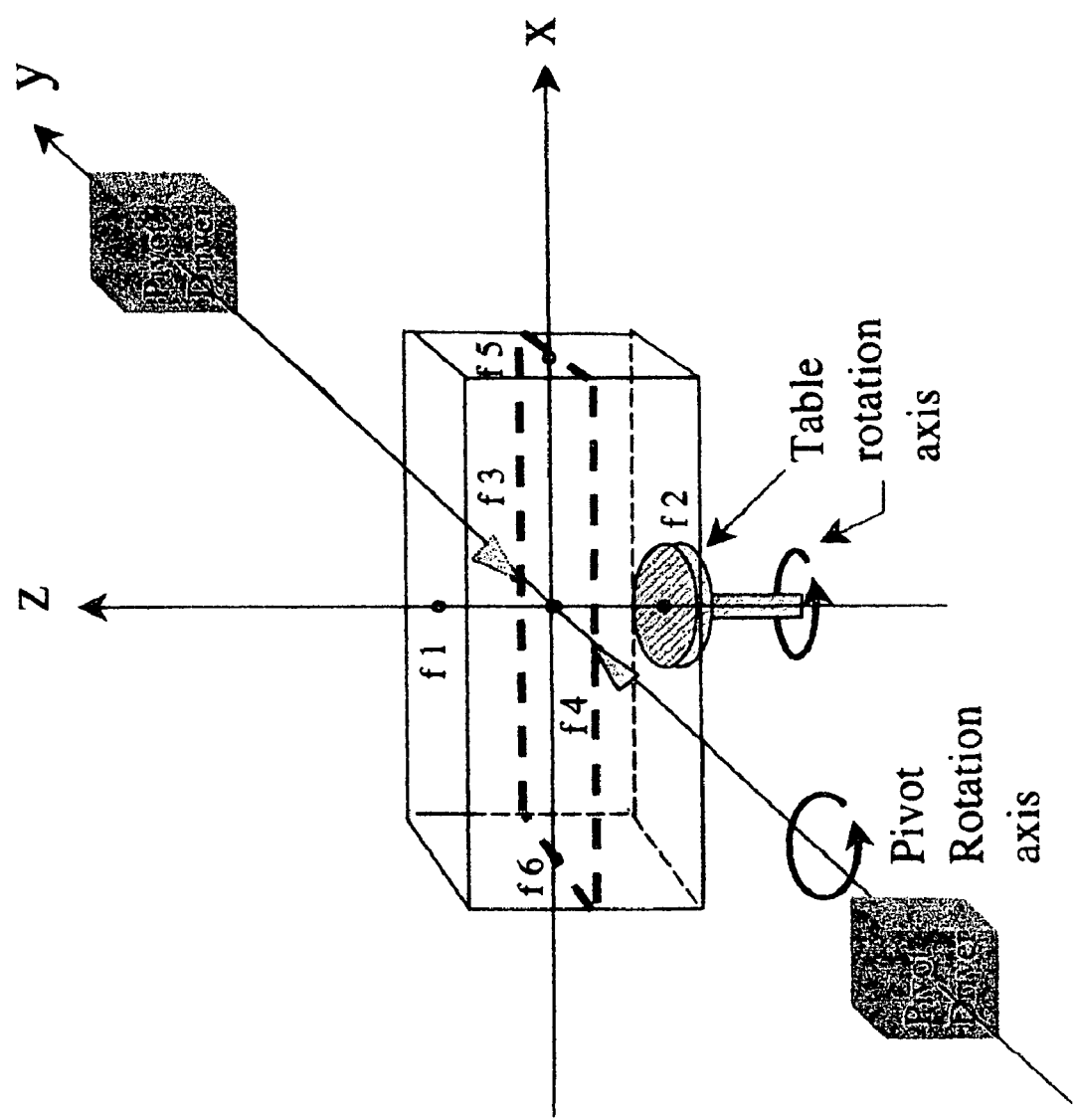

FIG. 11 For application B

Schematic drawing of the pivots with the object, assumed to be a rectangular parallelepiped for purposes of illustration, in the position of Step 1.

Figure 12:
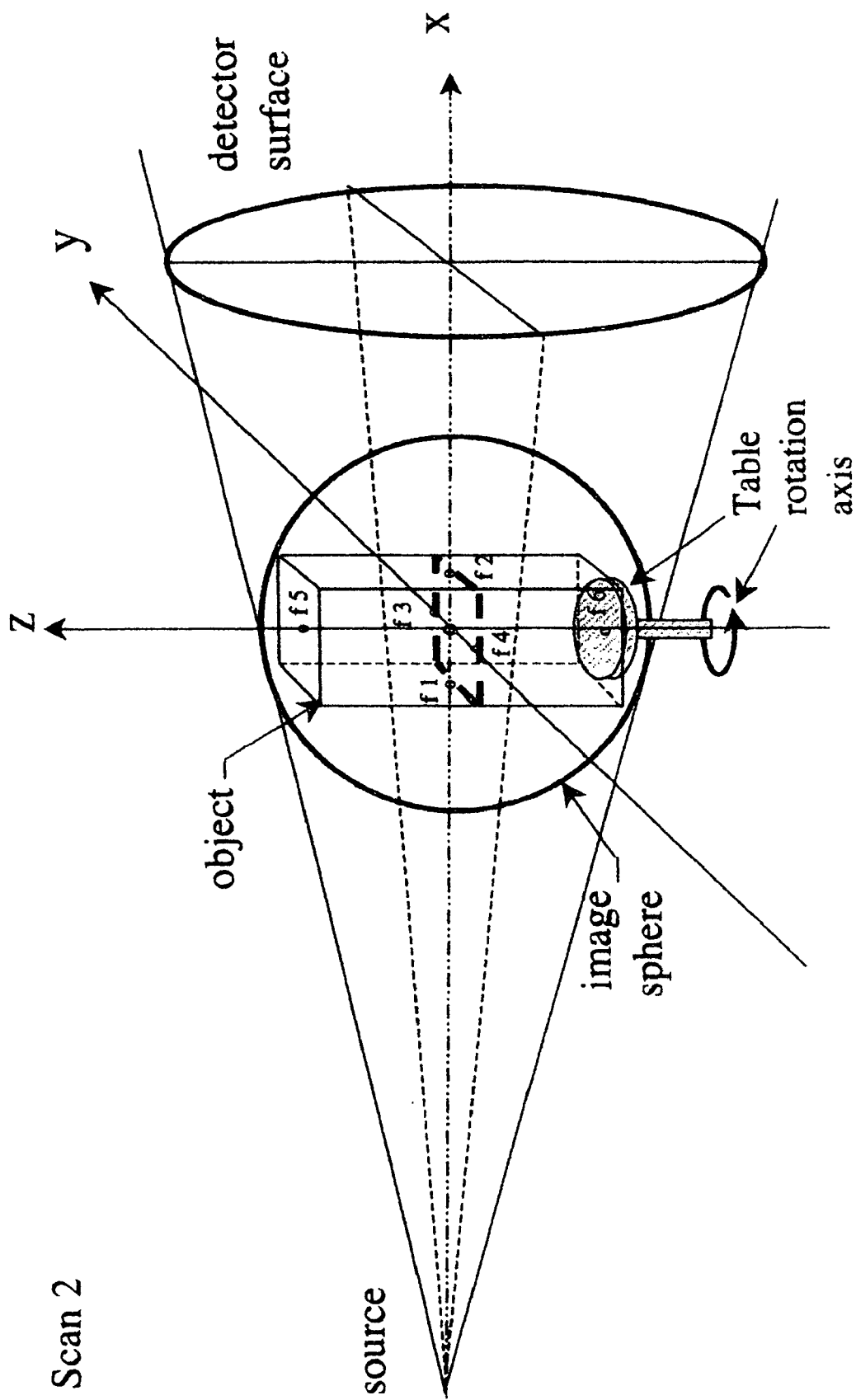

FIG. 12 For application B

Geometry for Step 3. The source-detector system remains stationery along the x-axis while the table supporting the object rotates about the z-axis.

Figure 13:
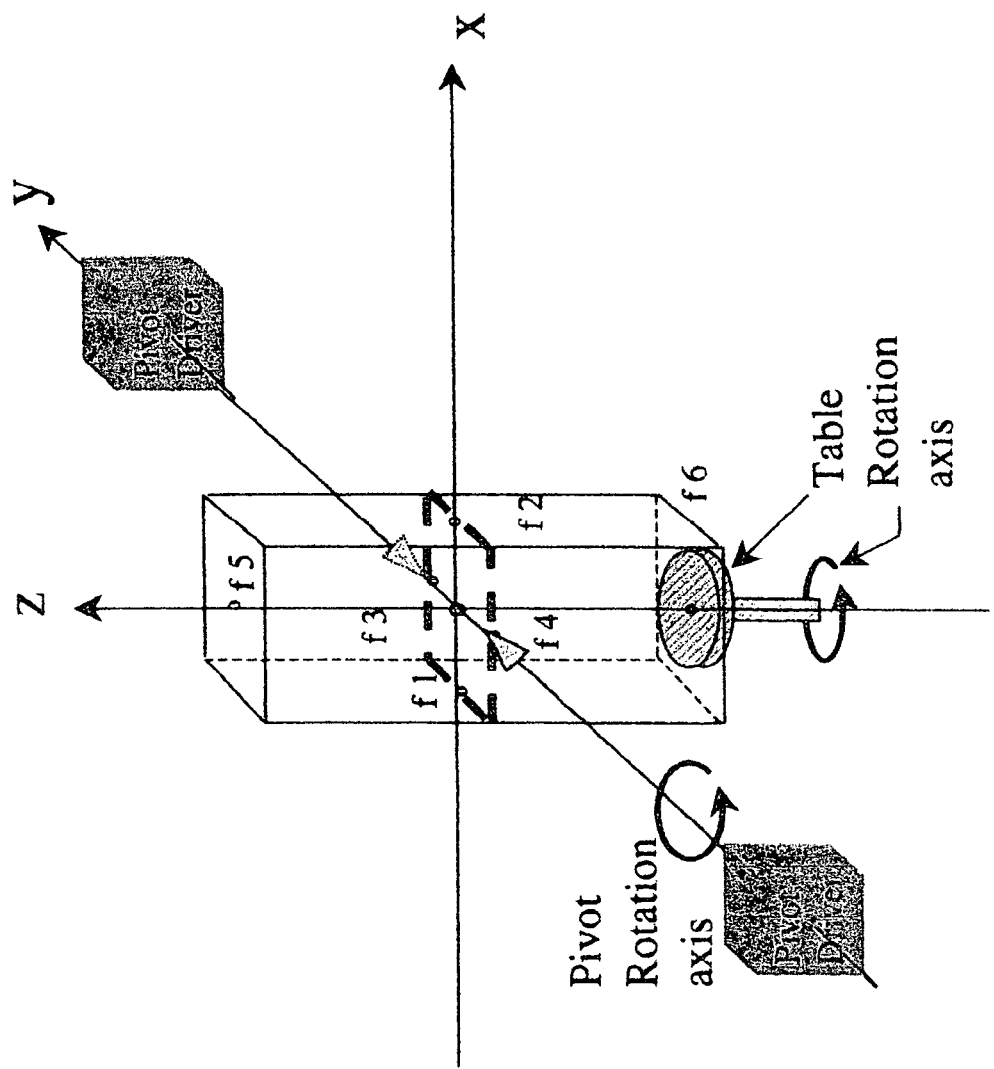

FIG. 13 For application B

After the object has been rotated through approximately 90° or 270° into the vertical direction about the y-axis with the pivots lying within the y-axis; the object is again rotated by the table for anywhere between (180°+cone angle) to 360° about the z-axis to obtain a second dataset.

I. APPLICATION TO INSPECTION OF BAGGAGE OR IMAGING OF LABORATORY ANIMALS

The algorithm developed in this application is for a case where the object remains throughout the procedure in a given horizontal plane. That is, the object can only rotate about a vertical axis but cannot be turned from horizontal into a vertical position. An example of such a setup is the security scanners for airport or office buildings, because the contents of the baggage may shift if the bag is turned from horizontal to vertical position thus giving inconsistent datasets. Another application of this is the cone beam CT scanner for imaging anaesthetized mouse for pharmaceutical purposes which also has to stay in a horizontal plane.

The object to be imaged is supported by a table which can rotate through 90° in the x-y plane about the z-axis. After this another rotation with the same gantry is performed in the same x-z plane about the y-axis.

The software of U.S. Pat. No. 5,375,156 of Kuo-Petravic & Hupke, 1994, which uses a particular combination of Feldkamp's modification of the Convolution Backprojection theorem may be used for combining the 2 datasets to produce excellent image.

DETAILED DESCRIPTION OF THE INVENTION

In medical CT, almost all scanners use the fan beam reconstruction and a 3-D image can obtain from spiraling 2-D slices from moving the body slowly along the axis of the gantry. Our invention is a direct 3-D method, using a cone beam source and a 2-D detector surface.

There are Several Advantages of our Cone Beam Method:
Our algorithm is simple and efficient compared to the current
  cone beam multi-slice method used in medical CT scanners. Hence our reconstruction software is faster and more
  accurate because there are no interpolations needed to
  combine the slices.
An order of magnitude faster data acquisition. Since we
  image the whole of the object in one go, only 2 gantry
  rotations are necessary instead of something like 30
  rotations for 2-D sliced spiral CT.

Our method is very suitable for working in a conveyor mode, useful for baggage inspection where fast throughput is necessary.

Because of simplicity, our software and hardware will be much less expensive to develop and manufacture.

In this application one is most interested in the low contrast resolution, especially in the case of imaging mouse where one is interested in distinguishing organs with very close densities. In FIG. 7, we show a computer phantom consisting of a skull at 2000 HU inside of which a brain matter of 1000 HU and 5 thin 2 voxels thick circular disks of 1010 HU superposed onto the brain matter in a vertical (coronal) plane, that is (y, z) plane, to test the resolution of this system. In FIG. 8a, we show the standard Feldkamp reconstruction from one circle scan. FIG. 8b shows the reconstructed image using 2 circular scans (G2) as described in this section. If one adds another third scan orthogonal to the previous 2 scans (G3), the resolution is further improved—FIG. 8c. But this is of theoretical interest only for it is not practical to build 3 gantries. The results can also be seen in FIGS. 9a and 9b, where linear plots along the z direction show the improvement as we increase the number of scans. It may be seen from FIG. 9b that a relative attenuaton ratio of 1003 HU/1000 HU may be detected with the 2 consecutive Feldkamp algorithm (G2).

We can Divide the Procedure into 3 Steps:

Step 1

Figure 2:
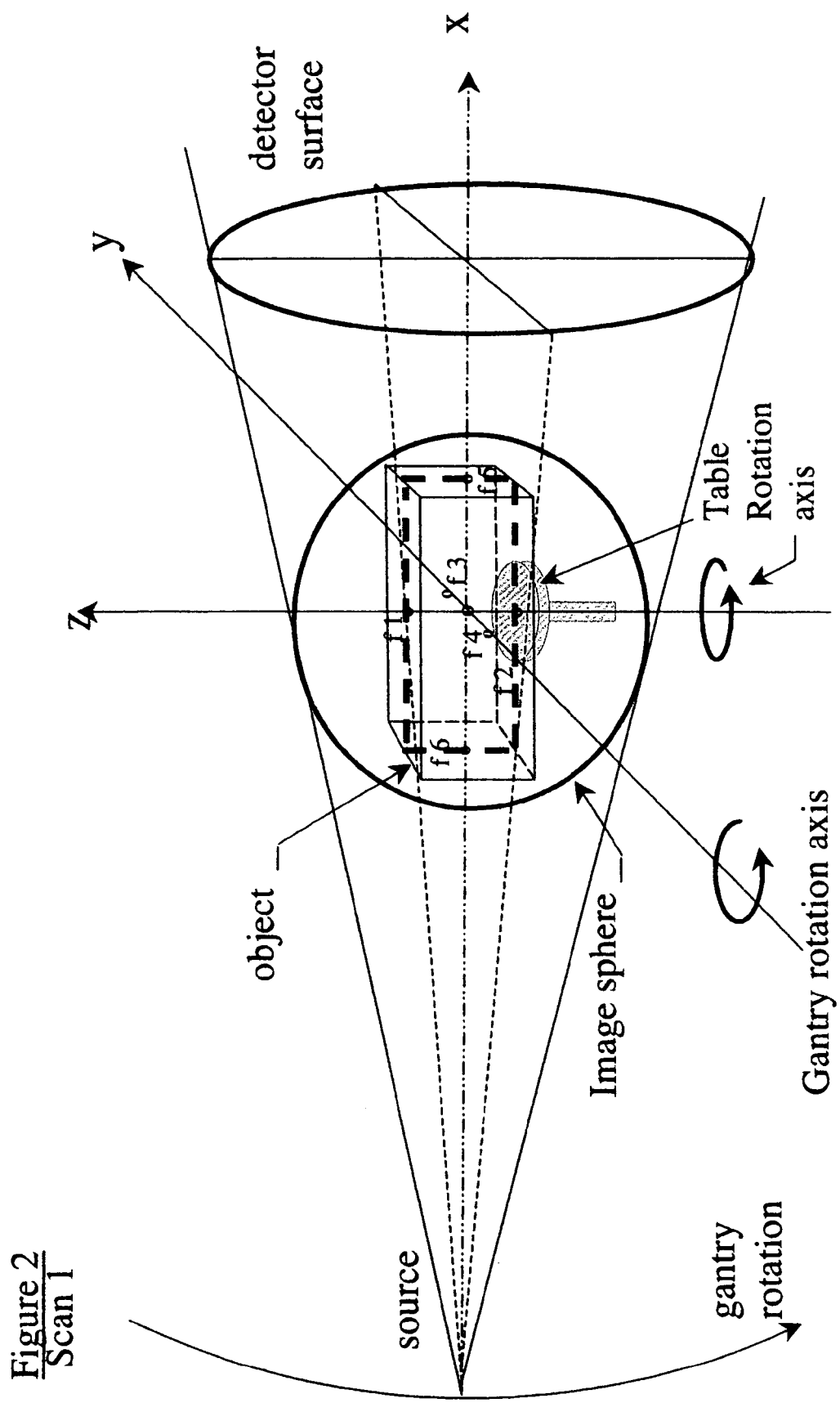
FIG. 2 For application A

This step follows the Feldkamp setup as shown in FIG. 2. The gantry rotates in the x-z plane about the y axis for a minimum of (180°+cone angle) and can have any value up to 360°. For better resolution, 360° of rotation is recommended because ¼-offset may be used to double the number of line integrals.

Using the example of a rectangular parallelepiped, FIG. 3 shows the relation of the object to the co-ordinate axes. The bold dashed line around the surface of the box indicate what is the midplane, (x, y=0, z) as given in Feldkamp algorithm. The 'tilted planes' of Feldkamp are planes to the either side of the midplane with small values of y. It can be seen that most line integrals collected in this dataset will be in or near the x-z plane and none would have large values of y. In other words, the resulting reconstruction will give good resolution in regions close to the midplane, which, for purposes of illustration, is over the 'long' dimension of the object which lies along the x-axis.

We use here the same algorithm as the standard Feldkamp, that is a 3-D modification of the standard 2-D Convolution Backprojection algorithm, and backproject onto the 3-D computational grid points covering the object.

Step 2

After gantry rotation of Step 1, we rotate the object through near 90° or 270° within the horizontal plane about the vertical z axis by means of the rotating table. FIG. 5.

Step 3

Here, we invoke the property that rotation of the object in a horizontal plane through 90° or 270° is the same as rotating the gantry through 90° or 270°.

The object now has its 'long' side along the y-axis, FIG. 4. A second dataset is obtained with another gantry rotation always keeping the gantry location fixed in the position as in Step 1, which is in the (x-z) plane. It is clear from FIGS. 4 & 5 that the new midplane, shown by a bold dashed line, will produce line integrals over the 'short' dimension of the object which are mostly orthogonal to the line integrals produced by step 1, hence we will have in the second scan good reconstruction over the 'short' dimension of the object.

Finally, the 2 datasets have to be combined in a specific way while making sure of the correspondence between the mesh points of one relative to the other to obtain the final image.

In FIG. 7, we show a computer phantom consisting of a skull of 2000 HU attenuation, inside of which a brain matter of 1000 HU and 5 thin, 2 voxels thick circular disks of 10 HU superposed onto the brain matter of 1000 HU in a coronal plane, that is (y, z) plane, to test the resolution of this system. In FIG. 8a, we show the standard Feldkamp reconstruction from one circle scan. FIG. 8b shows the reconstructed image using 2 circular scans (G2) as described in this section. If one adds another scan orthogonal to the previous 2 scans (G3), the resolution is further improved, FIG. 8c. The results can also be seen in FIGS. 9a and 9b, where linear plots along the z direction show the improvement as we increase the number of scans.

II. Application to Testing of Solid Objects

In this application, the rotating gantry is replaced by just one cone beam source and one 2-D detector surface, both staying fixed for purposes of illustration on the x-axis throughout the procedure. The costly rotating gantry with its associated electrical and mechanical components are eliminated. This is replaced by rotating the object which mathematically is equivalent to the rotation of the source-detector assembly, thus leading to a much simpler system at lower cost. In the first rotation, the object of study lies on a rotating horizontal table which can be rotated slowly about the z-axis, equivalent to a gantry rotating in the x-y plane about the z axis. Then the object is turned through 90° in the (x, z) plane about the y-axis by means of a pair of pivots on the y axis and another rotation of object about the z-axis is performed.

DETAILED DESCRIPTION OF THE INVENTION

Up to now, a CT platform for the nondestructive testing of solid materials uses the fan beam setup. It consists of a stationery fan beam source and a line of stationery detectors, with the object rotating about z-axis as well as moving slowly along the z-axis. A 3-D image is rendered by a composition of images in slices. Our invention is a direct 3-D method, using a cone beam source and a 2-D detector surface. The object is again rotating in x-y plane but the vertical motion is eliminated because the cone beam shines on the whole object in one go. There are several advantages of our cone beam method:

Our algorithm is simple and efficient compared to the currently used method of composing the 3-D image from many 2-D slices Hence our reconstruction software is both faster and more accurate because there are no interpolations needed to combine the slices.

An order of magnitude faster in data acquisition. Since we image the complete object in one go, only 2 rotations of the table are necessary with a special rotation of the object through 90° by means of pivots. So instead of something like 30 rotations for 2-D sliced spiral CT we can do it in the time of approximately 3 rotations of the table.

Our method is very suitable for working in a conveyor mode where fast throughput is required.

The object under test should be packed tightly into a precision made box which, for purposes of illustration, we assume to be a rectangular parallelepiped with 6 accurate perpendicular sides, which are marked f1 to f6, whose centers are marked by open dots, FIG. 10. The empty space inside the box has to be filled with some filling material such that the object remains absolutely fixed when turned from a horizontal to vertical position.

We can Divide the Procedure into 3 Steps:

Step 1

This step follows the Feldkamp setup as shown in FIG. 10. We keep the source-detector assembly fixed pointing along the x-axis throughput the procedure. for ease of pivoting the center of gravity of the box should be put at the origin (x=0, y=0, z=0), which is also the center of rotation of the table. The table is rotated slowly through anywhere between (180°+cone angle) to 360° about the z-axis, while a dataset is collected. For better resolution, 360° is recommended because ¼-offset may be used to double the number of line integrals in the scan.

FIG. 11 shows the relation of the box object to the coordinate axes. The bold dashed line around the surface of the box marks what is the midline, (x, y, z=0), which lies in the x-y plane of Feldkamp's algorithm. The 'tilted planes' of Feldkamp are planes to the either side of the midline with small values of z. It can be seen that most line integrals collected in this dataset 1 will be in or near the x-y plane and none would have large values of z. In other words, the resulting reconstruction will only be accurate in the region close to that of the midplane, which is, for purposes of illustration, over the 'long' dimension of the object lying along the x axis.

We use here the same algorithm as in the standard Feldkamp, that is a modification of the standard 2-D Convolution Backprojection algorithm, and backproject onto the 3-D rectangular mesh points of the object.

Step 2

FIG. 11 shows 2 pivot joints lying in the y axis centered about the 2 faces, f3 and f4, of the box. The pivot line, aligned to pass through the center of the system, (x=0, y=0, z=0), is used to rotate the object about the y-axis for 90° or 270°. At the end of this operation, the 'long' dimension of the box is now aligned along the z-axis.

Step 3

Here, we invoke the property that rotation of the object through 90° or 270° is the same as rotating the gantry through 90° or 270° as depicted in the G-2 scan of U.S. Pat. No. 5,375,156 of Kuo-Petravic & Hupke, 1994, shown in FIG. 1.

The object now has its 'long' side along the z-axis, FIGS. 12 and 13. A second dataset 2 is obtained with another rotation of the table through anywhere between (180°+cone angle) to 360°. It is clear from FIG. 12, that the new midplane, shown by a bold dashed line, will give information over the 'short' dimension of the object and the line integrals are mostly orthogonal to those of dataset 1 in Step 1.

We can use the same computer code as in Step 1 to collect dataset 2. Finally each backprojected point calculated in this step has to be combined with the corresponding mesh point of the first dataset to obtain the final image.

What we claim as our invention is:

1. In a computer tomography (CT) system, including one cone beam x-ray source and opposing 2-D (two dimensional) x-ray detector assembly and an object which is being imaged, said system being operable for relative rotation between the said assembly and said object, a method for obtaining a group of 2-D projection datasets from which 3-D (three dimensional) or 2-D images are obtained of a portion or whole of the said object comprising the steps of:

providing relative rotation between said assembly and said object by means of a rotating gantry in a vertical plane, which rotates while keeping the relative positions of the source and detector fixed to each other, the axis of rotation of the gantry being a horizontal axis substantially perpendicular to said vertical plane and passing through the center of system, which is the intersection of the said horizontal axis with the line joining the source and detector assembly in said vertical plane of gantry, for scanning to obtain related 2-D projection data sets from which backprojection is used to produce a first 3-D image over a 3-D grid encompassing the whole of the said object;

providing a substantially 90° or 270° rotation of the said object in a horizontal plane passing through the said center of system about a vertical axis in said vertical plane passing through said center of system, while the said assembly remains in a fixed location in space;

providing relative rotation between said assembly and said object in said vertical plane by means of said rotating gantry, the axis of rotation of the gantry being a horizontal axis in said horizontal plane and substantially perpendicular to said vertical plane, for scanning to obtain 2-D projection data sets from which backprojection is used to produce a second 3-D image over the same said 3-D grid encompassing the whole of the said object;

processing by combining the said first and said second images for obtaining a 3-D grid of data representative of a portion or whole of said object.

2. The method of claim 1, wherein processing of said group of 2-D projection datasets resulting in a first image of the said object consists of the steps of a Feldkamp reconstruction algorithm employing convolution and backprojection.

3. The method of claim 1, wherein processing of said group of 2-D projection datasets resulting in a second image of said object consists of the steps of a Feldkamp reconstruction algorithm employing convolution and backprojection.

4. The method of claim 1, wherein said object is supported and rotated within said horizontal plane by a rotating table or other mechanical or electrical device.

5. The method of claim 1, wherein the step are used to image any object, alive or inanimate, which have to stay in a horizontal plane throughout said CT procedure.

6. In a CT system comprising a stationary cone beam x-ray source and opposing 2-D x-ray detector assembly and an object which is being imaged, said CT system being operable for rotation of said object about a vertical axis of rotation substantially perpendicular to the line joining the x-ray source and detector assembly which is the axis of the assembly, the intersection of the said axis of assembly and said vertical rotation axis being the center of the system, a method for obtaining a group of 2-D data sets from which 3-D or 2-D images are obtained of a portion or whole of the said object consisting the steps of:

providing rotation of said object centered around said center of system about a vertical axis passing through the said center of system and substantially perpendicular to the said axis of assembly which lies in a horizontal plane passing through the said center of system for anywhere between (180°+half cone angle) to 360° for scanning to obtain a group of 2-D projection datasets from which backprojection is used to produce a first 3-D image over a 3-D grid encompassing the whole of the said object;

providing rotation of said object, centered around the said center of system about a horizontal axis passing through the said center and substantially perpendicular to said axis of assembly and substantially perpendicular to the vertical axis of rotation of the table, through 90° or 270° by means of either a pair of pivots or any other mechanical means or electrical means;

providing a second rotation of said object centered around the said center of system about a vertical axis passing through the said center of system and substantially perpendicular to said axis of assembly which lies in a horizontal plane passing through the said center of system for anywhere between (180°+half cone angle) to 360° for scanning to obtain a group of 2-D projection datasets from which backprojection is used to produce a second 3-D image over said 3-D grid encompassing the whole of the said object;

processing by combining the said first and said second 3-D images for obtaining a 3-D mesh of data representative of a portion or whole of said object to obtain the final image of the said object.

7. The method of claim 6, wherein processing of the said first 2D projection data resulting in a first 3-D image of the said object consists of the steps of a Feldkamp reconstruction algorithm employing convolution and backprojection.

8. The method of claim 6, wherein processing of the said second 2-D projection data resulting in a second 3-D image of the said object consists of the steps of a Feldkamp reconstruction algorithm employing convolution and backprojection.

9. The method of claim 6, wherein said object is supported and rotated in said horizontal plane by a rotating table or other mechanical or electrical device.

* * * * *